(12) United States Patent
Khalaj

(10) Patent No.: US 10,799,670 B2
(45) Date of Patent: Oct. 13, 2020

(54) EXPANDABLE SLEEVE FOR A CATHETER ASSEMBLY

(71) Applicant: Avent, Inc., Alpharetta, GA (US)

(72) Inventor: Steve S. Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 198 days.

(21) Appl. No.: 15/735,742

(22) PCT Filed: Jun. 18, 2015

(86) PCT No.: PCT/US2015/036369
§ 371 (c)(1),
(2) Date: Dec. 12, 2017

(87) PCT Pub. No.: WO2016/204761
PCT Pub. Date: Dec. 22, 2016

(65) Prior Publication Data
US 2018/0185613 A1    Jul. 5, 2018

(51) Int. Cl.
*A61M 25/00* (2006.01)
*A61M 25/06* (2006.01)

(52) U.S. Cl.
CPC .... *A61M 25/0023* (2013.01); *A61M 25/0097* (2013.01); *A61M 25/0606* (2013.01); *A61M 2025/0024* (2013.01); *A61M 2025/0098* (2013.01); *A61M 2025/0681* (2013.01); *A61M 2205/0266* (2013.01)

(58) Field of Classification Search
CPC .......... A61M 25/0023; A61M 25/0606; A61M 25/0097; A61M 2205/0266; A61M 2025/0681; A61M 2025/0024; A61M 2025/0098
See application file for complete search history.

(56) References Cited

U.S. PATENT DOCUMENTS 3,547,119 A    12/1970   Hall et al.
4,160,450 A     7/1979   Doherty
4,323,065 A     4/1982   Kling
(Continued)

FOREIGN PATENT DOCUMENTS

EP    0 588 546 A2    3/1994
EP    2 574 362 A1    4/2013
(Continued)

OTHER PUBLICATIONS

International Search Report for PCT/US2015/036369, dated Feb. 18, 2016, 4 pages.

*Primary Examiner* — Amber R Stiles
(74) *Attorney, Agent, or Firm* — Dority & Manning, P.A.

(57) ABSTRACT

The present disclosure is directed to an expandable sleeve for a catheter assembly. The expandable sleeve includes a body configured to fit coaxially around an outer diameter of a catheter of the catheter assembly at a transition location between a hub and the catheter. Further, the body of the sleeve includes a length extending from a first end to a second end. As such, the sleeve is expandable between a compressed position and an expanded position so as to prevent the catheter from collapsing along the length of the sleeve. In addition, when in the expanded position, at least a portion of an interior surface of the sleeve contacts an outer diameter of the catheter.

18 Claims, 4 Drawing Sheets

(56) References Cited

U.S. PATENT DOCUMENTS

| | | |
|---|---|---|
| 4,762,516 A | 8/1988 | Luther et al. |
| 4,828,549 A | 5/1989 | Kvalo |
| 4,985,022 A | 1/1991 | Fearnot et al. |
| 5,058,570 A | 10/1991 | Idemoto et al. |
| 5,466,230 A | 11/1995 | Davila |
| 5,531,713 A | 7/1996 | Mastronardi et al. |
| 5,853,393 A | 12/1998 | Bogert |
| 8,303,570 B2 | 11/2012 | Gregorich et al. |
| 8,611,993 B2 | 12/2013 | Vitullo et al. |
| 2002/0052576 A1* | 5/2002 | Massengale ...... A61M 25/0069 604/164.01 |
| 2003/0153873 A1 | 8/2003 | Luther et al. |
| 2004/0243205 A1 | 12/2004 | Keravel et al. |
| 2005/0090801 A1 | 4/2005 | Racz et al. |
| 2005/0107739 A1 | 5/2005 | Palma |
| 2005/0283148 A1 | 12/2005 | Janssen et al. |
| 2006/0224223 A1 | 10/2006 | Podhajasky et al. |
| 2008/0009831 A1 | 1/2008 | Griffin |
| 2009/0099590 A1 | 4/2009 | Wijeratne et al. |
| 2009/0187140 A1 | 7/2009 | Racz |
| 2010/0160863 A1 | 6/2010 | Heuser |
| 2010/0241060 A1 | 9/2010 | Roizman et al. |
| 2012/0071937 A1 | 3/2012 | Sundaramurthy et al. |
| 2013/0116651 A1* | 5/2013 | Takagi ............. A61M 25/0097 604/506 |
| 2014/0142509 A1* | 5/2014 | Bonutti ............. A61B 17/3439 604/164.03 |
| 2014/0275926 A1 | 9/2014 | Scott et al. |
| 2014/0316268 A1 | 10/2014 | Kafiluddi et al. |
| 2015/0157228 A1 | 6/2015 | Marino et al. |
| 2015/0352333 A1 | 12/2015 | Arellano Cabrera et al. |
| 2015/0360003 A1 | 12/2015 | Khalaj |
| 2015/0360005 A1 | 12/2015 | Arellano Cabrera et al. |
| 2016/0206363 A1 | 7/2016 | Mehta et al. |

FOREIGN PATENT DOCUMENTS

| | | |
|---|---|---|
| FR | 2684006 A1 | 5/1993 |
| WO | WO 2009/091567 A2 | 7/2009 |
| WO | WO 2014/074237 A1 | 5/2014 |

\* cited by examiner

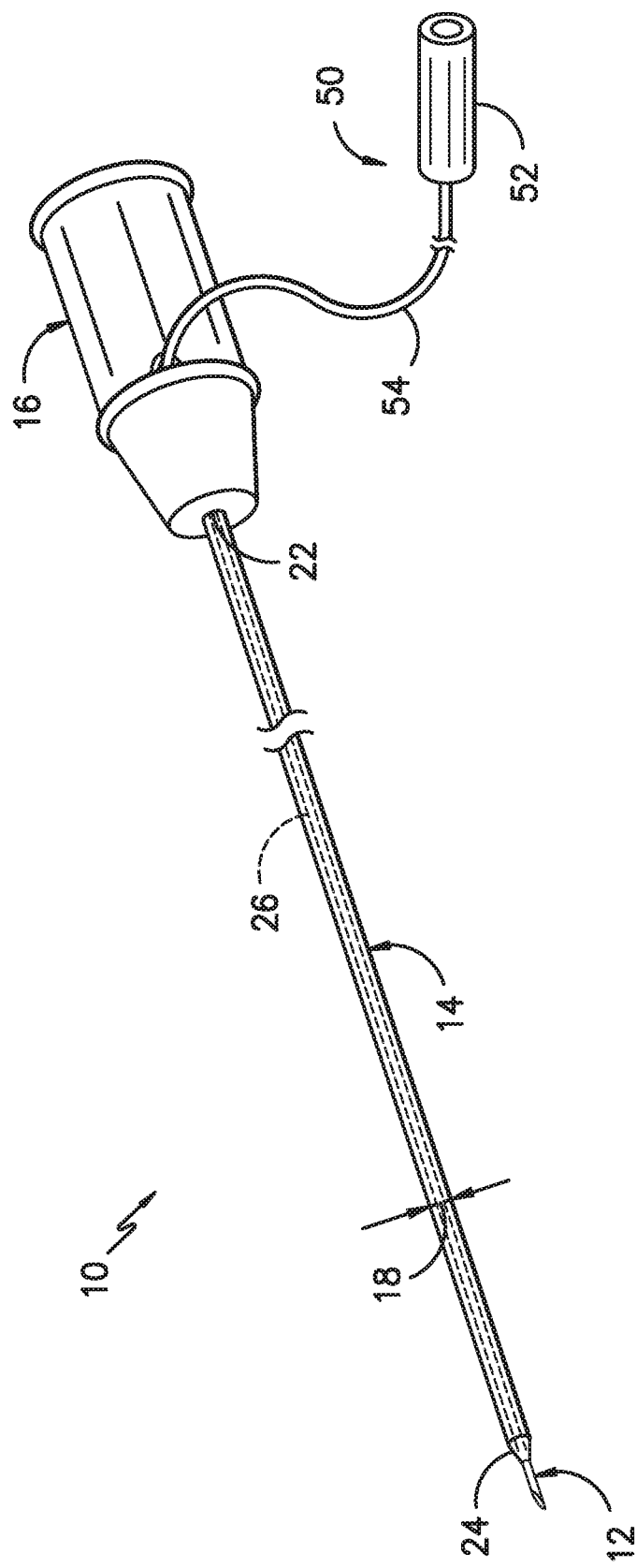
FIG. -1-

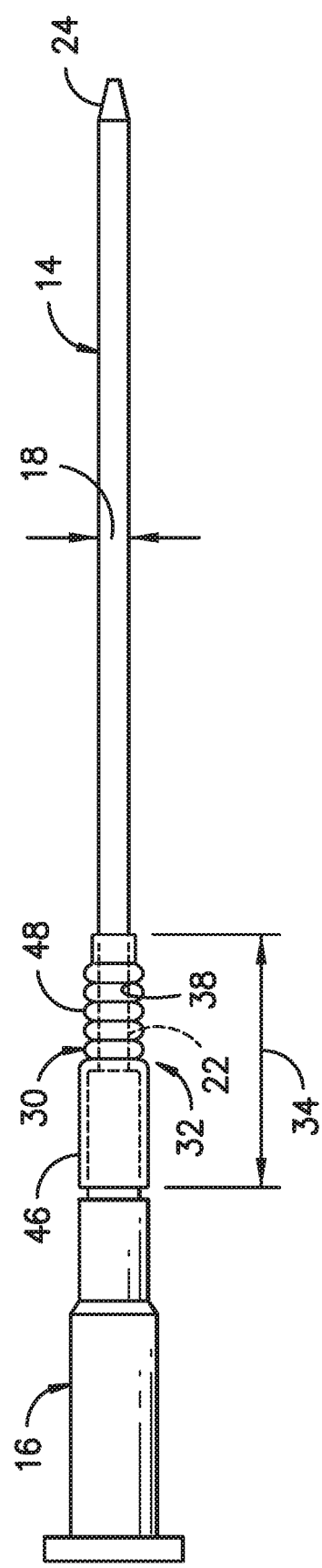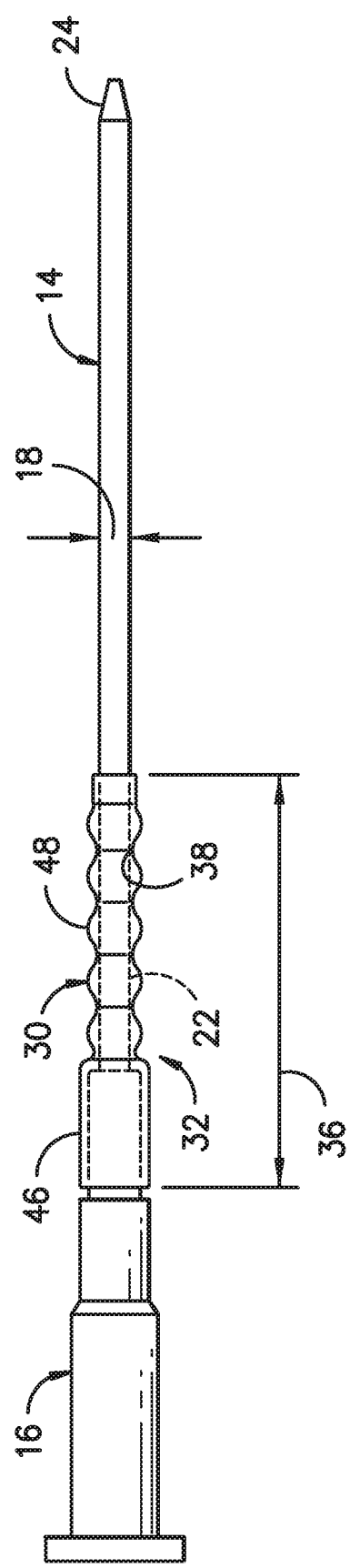

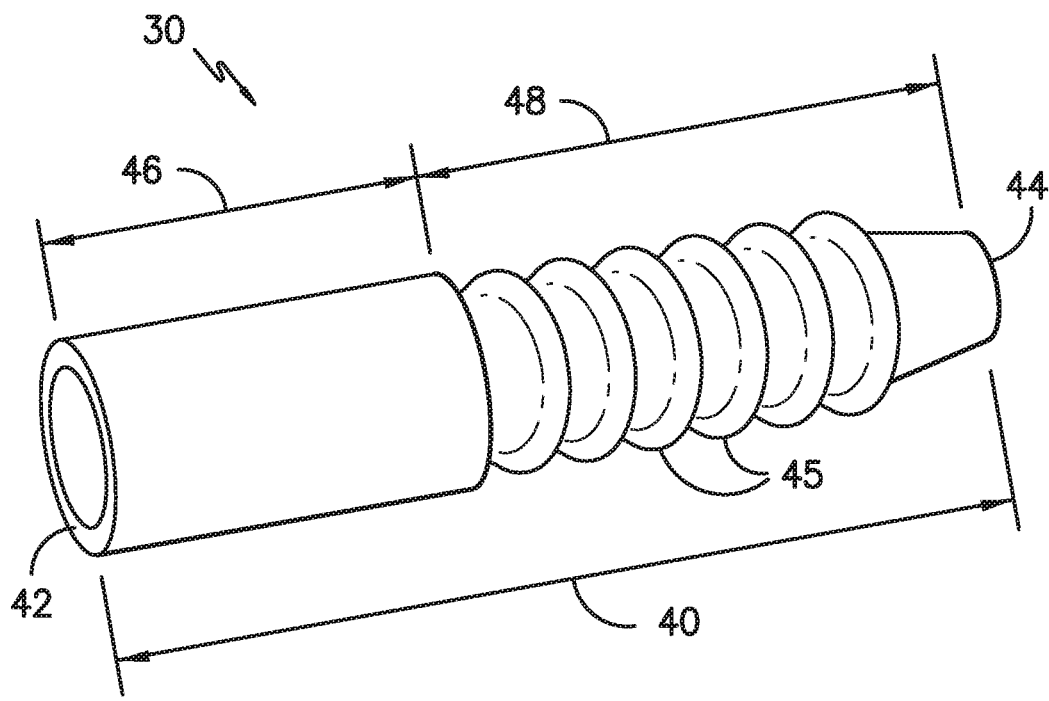
FIG. -4-
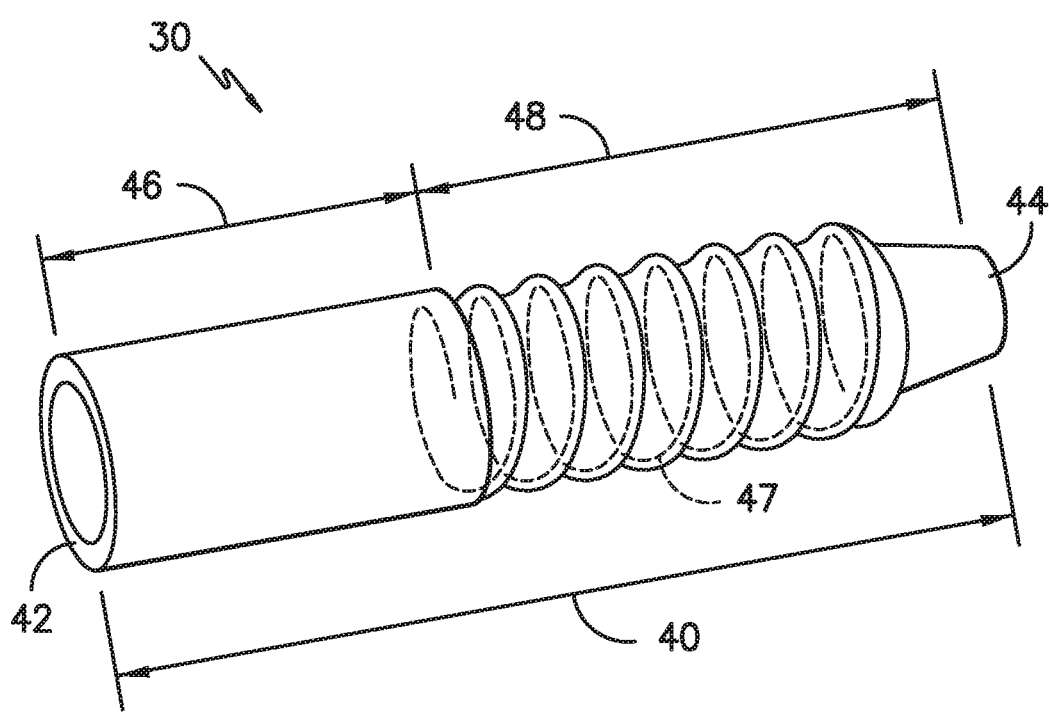
FIG. -5-

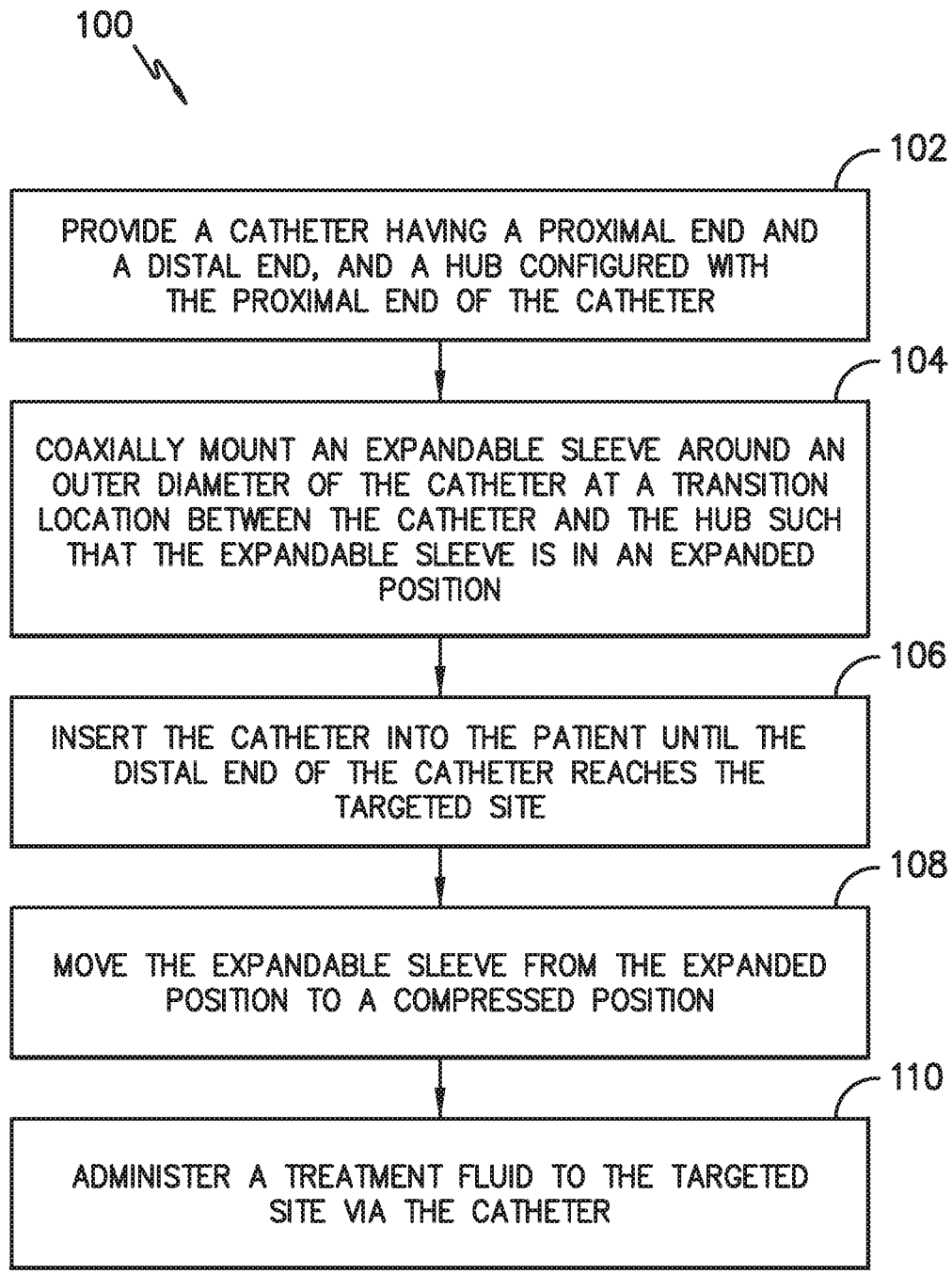
FIG. -6-

EXPANDABLE SLEEVE FOR A CATHETER ASSEMBLY

RELATED APPLICATIONS

The present application claims priority to International Application Number PCT/US2015/036369 filed on Jun. 18, 2015, which is incorporated herein in its entirety by reference hereto.

FIELD OF THE INVENTION

The present invention relates generally to the field of medical catheters and more particularly to an expandable sleeve for a catheter that prevents kinking of the catheter.

BACKGROUND

Devices used to administer a fluid inside the anatomy of a patient are well known. For example, hypodermic needles, catheters, and the like are often used to deliver medication and other fluids to targeted sites within the body. In many instances, catheters are preferred because they can deliver fluid to a particular site over a period of time. Since catheters are generally made of a flexible plastic material, a needle is typically used to insert the catheter within a patient. For example, certain catheters, generally referred to as "through-the-needle" catheters, often require stiff, hollow introducer needles for placement within the anatomy. Thus, the catheter can be inserted through the needle after the needle is located at the targeted site. Typically, such introducer needles have sharp tips that may damage tissue and/or nerves during their delivery into a body, thus causing discomfort for the patient.

Another type of catheters, generally referred to as "over-the-needle" (OTN) catheters, include a catheter coaxially mounted onto a needle. In this type of catheter, the catheter and the needle may be inserted into a patient together. Once the catheter and the needle are located at the targeted site, the needle can be removed, leaving the catheter in place. Thus, OTN catheters can be purposely directed to a targeted site within a patient without the need to thread the catheter therethrough. Accordingly, OTN catheters have gained increased attention in regard to delivering anesthetic medication, for example, for the purposes of nerve block.

It is desired to design OTN catheters with thin walls so as to decrease discomfort to the patient and to minimize leakage at the insertion site of the catheter. Such thin walls, however, can increase the catheter's susceptibility to kinking or collapsing when being inserted within a patient. For example, some OTN catheters are known to bend or kink at the transition location between the hub and the catheter.

Accordingly, the present invention is directed to an expandable sleeve for a catheter that addresses the aforementioned issues.

SUMMARY OF THE INVENTION

Objects and advantages of the invention will be set forth in part in the following description, or may be obvious from the description, or may be learned through practice of the invention.

In one aspect, the present invention is directed to an over-the-needle (OTN) catheter assembly. The catheter assembly includes a catheter, a hub, a needle, and an expandable sleeve. The catheter has a body that defines an outer diameter. Further, the body includes a proximal end and a distal end and defines a lumen extending from the proximal end to the distal end. The hub is configured with the proximal end of the catheter. The needle is configured within the lumen of the catheter. Further, the needle generally extends from the proximal end to the distal end. The expandable sleeve is coaxially mounted onto the outer diameter of the catheter at a transition location between the hub and the catheter. Moreover, the expandable sleeve is expandable between a compressed position and an expanded position. Thus, when in the expanded position, at least a portion of an interior surface of the expandable sleeve contacts the outer diameter of the body of the catheter so as to prevent kinking or bending of the catheter.

In one embodiment, the expandable sleeve may include a first portion and a second portion. More specifically, the first portion may be configured with the hub and the second portion may be configured with the catheter. In certain embodiments, the first portion of the sleeve is configured to fit over a portion of the hub. For example, the expandable sleeve may include a total length extending from a first end to a second end. Thus, in such an embodiment, the first end of the expandable sleeve may be fixed to the hub. In addition, the second end of the expandable sleeve may be tapered. As such, the second end of the sleeve may be inserted into a patient thereby preventing fluid leakage from the patient. In particular embodiments, the second portion of the sleeve may include a plurality of bellows that allow the sleeve to expand between the compressed position and the expanded position. Alternatively, the second portion of the sleeve may include a coil member that allows the sleeve to expand between the compressed position and the expanded position. Thus, the compressed position of the expandable sleeve is configured to maximize a catheter penetration length into a patient. In addition, the sleeve is configured to prevent the catheter from collapsing along the length of the sleeve.

In further embodiments, at least a portion of the expandable sleeve may include a shape-memory material. For example, the shape-memory material may include a shape-memory polymer, a shape-memory alloy, or similar. More specifically, the shape-memory polymer may include block copolymers, thermoplastic polymers, thermosetting polymers, or similar. Further, the shape-memory alloy may include Nitinol. In such embodiments, the catheter assembly may also include a heat application assembly configured to apply heat to the expandable sleeve such that the sleeve expands from the compressed position to the expanded position.

In another aspect, the present disclosure is directed to an expandable sleeve for use with a catheter assembly. The sleeve includes a body configured to fit coaxially around an outer diameter of a catheter of the catheter assembly at a transition location between a hub and the catheter. Further, the body of the sleeve includes a length extending from a first end to a second end. As such, the sleeve is expandable between a compressed position and an expanded position so as to prevent the catheter from collapsing along the length of the sleeve. In addition, when in the expanded position, at least a portion of an interior surface of the sleeve contacts an outer diameter of the catheter.

In yet another aspect, the present disclosure is directed to a method for using a catheter assembly to provide treatment to a targeted site within a patient. The method includes providing a catheter having a proximal end and distal end. Another step includes coaxially mounting an expandable sleeve around an outer diameter the catheter at a transition location between the catheter and the hub such that the expandable sleeve is in an expanded position. The method further includes inserting the catheter into the patient until the distal end of the catheter reaches the targeted site. A further step includes moving the expandable sleeve from the expanded position to a compressed position. The method also includes administering a treatment fluid to the targeted site via the catheter.

In one embodiment, the catheter assembly may include an over-the-needle (OTN) catheter assembly. In such an embodiment, the catheter may be coaxially mounted onto a needle. In addition, the catheter and the needle are secured together via the hub. The method further includes inserting simultaneously the catheter and the needle into the patient until the distal end of the catheter reaches the targeted site. Thus, in additional embodiments, the method may also include removing the needle from the catheter while the catheter remains within the patient adjacent to the targeted site before administering the treatment fluid.

In another embodiment, the method may also include fitting a first portion of the expandable sleeve over a portion of the hub and fitting a second portion of the expandable sleeve over the outer diameter of the catheter. In another embodiment, the expandable sleeve includes a total length extending from a first end to a second end. Thus, the sleeve is configured to prevent the catheter from collapsing along the length of the sleeve. As such, in certain embodiments, the method may also include fixing a first end of the expandable sleeve to the hub. In additional embodiments, the second portion of the expandable sleeve may include a plurality of bellows that allow the sleeve to expand between the compressed position and the expanded position. Alternatively, the second portion of the sleeve may include a coil member that allows the sleeve to expand between the compressed position and the expanded position. Thus, the compressed position is configured to maximize a catheter penetration length.

In further embodiments, the step of moving the expandable sleeve from the expanded position to the compressed position further may include manually moving the expandable sleeve from the expanded position to the compressed position, e.g. a user can manually slide the sleeve between the expanded position and the compressed position.

Further, as mentioned, at least a portion of the expandable sleeve may include a shape-memory material. Thus, in such embodiments, the step of moving the expandable sleeve from the expanded position to the compressed position may include applying heat to the expandable sleeve. More specifically, in certain embodiments, the step of applying heat to the expandable sleeve may include at least one of the following: generating a current through the sleeve via a nerve stimulation assembly, generating a current through the expandable sleeve via one or more battery devices, submerging at least a portion of the expandable sleeve into a temperature-controlled water, generating friction near the expandable sleeve, generating vibration near the expandable sleeve via an ultrasound device, or similar.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an over-the-needle (OTN) catheter assembly according to the present disclosure;

FIG. 2 illustrates a side view of one embodiment of a catheter assembly according to the present disclosure, particularly illustrating an expandable sleeve in a compressed position;

FIG. 3 illustrates a side view of one embodiment of a catheter assembly according to the present disclosure, particularly illustrating an expandable sleeve in an expanded position;

FIG. 4 illustrates a perspective view of one embodiment of an expandable sleeve according to the present disclosure;

FIG. 5 illustrates a perspective view of another embodiment of an expandable sleeve according to the present disclosure; and FIG. 6 illustrates a flow diagram of one embodiment of a method for using an OTN catheter assembly having an expandable sleeve to provide treatment to a targeted site within a patient in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to an expandable sleeve for an over-the-needle (OTN) catheter assembly that prevents the catheter from collapsing, e.g. at a transition location between the hub and the catheter. More specifically, the expandable sleeve is coaxially mounted onto an outer diameter of the catheter at a transition location between the hub and the catheter. Further, the expandable sleeve is expandable between a compressed position and an expanded position. In addition, when in the expanded position, at least a portion of an interior surface of the expandable sleeve contacts the outer diameter of the body of the catheter. By contacting the outer diameter of the catheter, the expandable sleeve prevents kinking or bending at the transition location between the hub and the catheter. Further, by providing a sleeve that expands and contracts, the sleeve is capable of maximizing an effective catheter length, i.e. the catheter penetration length into a patient.

Referring now to the drawings, various views of one embodiment of an over-the-needle (OTN) catheter assembly 10 and expandable sleeve 30 according to the present disclosure are illustrated in FIGS. 1-5. For example, as shown, the OTN catheter assembly 10 includes catheter 14 having a body 20 defining an outer diameter 18 that extends between a proximal end 22 and distal end 24. Further, the catheter 14 is coaxially mounted onto a needle 12. Thus, the OTN catheter assembly 10 is configured such that the catheter and needle can be simultaneously inserted into a patient. In addition, the body 20 of the catheter 14 defines a lumen 26 extending from the proximal end 22 of the catheter 14 to the distal end 24. Thus, the catheter 14 is configured to deliver a treatment fluid to a targeted site within the patient via the lumen 26. More specifically, in certain embodiments, the proximal end 22 of the catheter 14 may include a hub 16 configured thereon for mating communication with a fluid delivery device (not shown) such that a treatment fluid can be delivered to a targeted site within a patient via the lumen 26 of the catheter 14. As mentioned, the fluid delivery device may be any suitable device known in the art, such as a pump, reservoir, syringe, or the like. Further, the hub 16 may have any conventional configuration, such as a Luer-lock fitting. It should also be understood that the present disclosure may utilize other types of catheter assemblies in addition to OTN catheter assemblies. For example, in certain embodiments, a through-the-needle catheter assembly may be employed.

Referring particularly to FIGS. 2-5, the catheter assembly 10 also includes an expandable sleeve 30 coaxially mounted onto the outer diameter 18 of the catheter 14 at a transition location 32 between the hub 16 and the catheter 14. Further, the expandable sleeve 30 is expandable between a compressed position 34 (FIG. 2) and an expanded position 36 (FIG. 3). Thus, when in the expanded position 36, at least a portion of an interior surface 38 of the expandable sleeve 30 contacts the outer diameter 18 of the body 20 of the catheter 14. For example, as shown, the interior surface 38 of the expandable sleeve 30 contacts the outer diameter 18 of the body 20 of the catheter 14 at a plurality of locations. By contacting the catheter 14, the sleeve 30 helps to prevent kinking at the transition location 32 (i.e. between the hub 16 and the catheter 14).

More specifically, as shown in FIGS. 4 and 5, the expandable sleeve 30 includes a first portion 46 and a second portion 48. Thus, as shown in FIGS. 2 and 3, the first portion 46 of the sleeve 30 may be configured with the hub 16. More specifically, the first portion 46 may be fitted around at least a portion of the hub 16. In addition, as shown, the expandable sleeve 30 defines a total length 40 extending from a first end 42 to a second end 44. Thus, the first end 42 of the expandable sleeve 30 may be fixed to the hub 16. For example, in certain embodiments, the first end 42 of the sleeve 30 may be secured to the hub 16 via an interference fit, adhesive, or similar. Further, the second end 44 of the sleeve 30 may be tapered. Thus, in such embodiments, the tapered second end 44 may have substantially the same outer diameter as the outer diameter 18 of the catheter 14. As such, the second end 44 of the expandable sleeve 30 can be easily inserted into a patient. Thus, the second end 44 of the sleeve 30 may be configured to prevent fluid leakage from the patient at the insertion site.

In further embodiments, the second portion 48 of the sleeve 30 may be configured with the catheter 14. More specifically, as shown in FIGS. 2 and 3, the second portion 48 of the sleeve 30 may be coaxially mounted around the outer diameter 18 of the catheter 14. Thus, the second portion 48 of the sleeve 30 is configured to move or slide along the outer diameter 18 of the catheter 12.

In particular embodiments, as shown in FIG. 4, the second portion 48 of the sleeve 30 may include a plurality of bellows 45 that allow the sleeve 30 to expand between the compressed position 34 and the expanded position 36. Thus, the compressed position 34 of the expandable sleeve 30 is configured to maximize a catheter penetration length into a patient. In alternative embodiments, as shown in FIG. 5, the second portion 48 of the sleeve 30 may include a coil member 47. For example, as shown, the coil member 47 may be formed into the shape of a helix that can be easily compressed (FIG. 2) and that can easily return to its natural length when unloaded (FIG. 3). Accordingly, the sleeve 30 as described herein is configured to prevent the catheter 14 from collapsing along the length 40 of the sleeve 30.

In additional embodiments, at least a portion of the expandable sleeve 30 may be constructed of include a shape-memory material. More specifically, the second portion 48 of the sleeve may be constructed of a shape-memory material. As used herein, a "shape-memory material" is generally defined as a light-weight material that has the ability to return from a deformed shape to its original shape when induced by an external trigger, such as a temperature change. Thus, in certain embodiments, shape-memory material essentially remembers its original shape such that when it is deformed, it is capable of returning to its pre-deformed shape when heated. It should be understood by those of ordinary skill in the art that the shape-memory material may include a shape-memory polymer, a shape-memory alloy, or similar. More specifically, in one embodiment, the shape-memory polymer may include at least one of block copolymers, thermoplastic polymers, thermosetting polymers, or similar. Alternatively, the shape-memory alloy may include nickel titanium, also known as Nitinol, which is a metal alloy of nickel and titanium or similar.

As such, in certain embodiments, the catheter assembly 10 may also include a heat application assembly 50 configured to apply heat to the expandable sleeve 30 such that the sleeve 30 moves between the compressed position 34 and the expanded position 36. For example, as shown in FIG. 1, the heat application assembly 50 may be coupled with the hub 16 of the catheter 14 so as to apply heat or current to the expandable sleeve 30. In further embodiments, the heat application assembly 50 may be directly coupled to the catheter 14 or the needle 12 or any other suitable component of the OTN catheter assembly 10. Further, as shown in FIG. 1, the heat application assembly 50 may correspond to a nerve stimulator apparatus having a nerve stimulator 52 that provides heat or current through one or more stimulator wires 54. Thus, when the stimulator wire 54 applies heat or current to the expandable sleeve 30, the second end 44 of the sleeve 30 expands to the expanded position 36. It should be understood, however, that the heat application assembly 50 can further include any other suitable heating assembly known in the art and the illustrated embodiment is provided for illustrative purposes only. For example, in further embodiments, the heat application assembly 50 may also include one or more battery devices, temperature-controlled water, an ultrasound device, a vibration device, or similar.

Referring now to FIG. 6, a flow diagram of one embodiment of a method 100 for using a catheter assembly as described herein so as to provide treatment to a targeted site within a patient is illustrated. As shown at 102, the method 100 includes providing a catheter having a proximal end and distal end and a hub 16 configured with the proximal end 22 of the catheter 14. As shown at 104, the method 100 includes coaxially mounting an expandable sleeve around an outer diameter the catheter at a transition location between the catheter and the hub such that the expandable sleeve is in an expanded position. As shown at 106, the method 100 includes inserting the catheter 14 into the patient until the distal end 24 of the catheter 14 reaches the targeted site. As shown at 108, the method 100 includes moving the expandable sleeve from the expanded position to a compressed position. As shown at 110, the method 100 includes administering a treatment fluid to the targeted site via the catheter.

In one embodiment, the catheter assembly may include an over-the-needle (OTN) catheter assembly, e.g. as shown in FIG. 1. In such an embodiment, the catheter 14 may be coaxially mounted onto a needle 12. In addition, the catheter 14 and the needle 12 may be secured together via the hub 16. Thus, the method 100 may include inserting simultaneously the catheter 14 and the needle 12 into the patient until the distal end 24 of the catheter 14 reaches the targeted site. Thus, in additional embodiments, the method 100 may also include removing the needle 12 from the catheter 14 while the catheter 14 remains within the patient adjacent to the targeted site before administering the treatment fluid.

In another embodiment, the method 100 may further include fitting a first portion 46 of the expandable sleeve 30 over a portion of the hub 16 and fitting a second portion 48 of the expandable sleeve 30 over an outer diameter of the catheter 14. More specifically, in another embodiment, the method 100 may also include fixing a first end 42 of the expandable sleeve 30 to the hub 16.

In further embodiments, the step of moving the expandable sleeve 30 from the expanded position 36 to a compressed position 34 may include manually moving the expandable sleeve 30 from the expanded position 36 to the compressed position 34. For example, a user can manually slide the sleeve between the expanded position 36 and the compressed position 34.

Alternatively, the step of moving the expandable sleeve 30 from the expanded position 36 to the compressed position 34 may include applying heat to the expandable sleeve 30. More specifically, in certain embodiments, the step 106 of applying heat to the catheter assembly may further include at least one of the following: generating a current through the catheter via a nerve stimulation assembly, generating a current through the catheter via one or more battery devices, submerging at least a portion of the catheter into temperature-controlled water, generating friction near the catheter, generating vibration near the catheter via an ultrasound device, or another other suitable heat application method.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An over-the-needle catheter assembly, comprising:
    a catheter comprising a body defining an outer surface having an outer diameter, the body extending in a longitudinal direction from a proximal end to a distal end, the body defining a lumen extending from the proximal end to the distal end;
    a hub configured with the proximal end of the catheter;
    a needle configured within the lumen of the catheter, the needle extending from said proximal end to said distal end; and,
    an expandable sleeve coaxially mounted onto the outer surface of the catheter at a transition location between the hub and the catheter, the expandable sleeve being expandable in the longitudinal direction between a compressed position and an expanded position, wherein, in the expanded position, at least a portion of an interior surface of the sleeve contacts the outer diameter of the body of the catheter,
    wherein the expandable sleeve comprises a first portion and a second portion, the first portion being configured with the hub and the second portion being configured with the catheter, wherein the second portion of the expandable sleeve comprises a plurality of bellows to allow the sleeve to expand between the compressed position and the expanded position, and wherein the compressed position maximizes a catheter penetration length.

2. The catheter assembly of claim 1, wherein the first portion of the expandable sleeve fits over a portion of the hub.

3. The catheter assembly of claim 1, wherein the expandable sleeve comprises a total longitudinal length extending from a first end to a second end, and wherein the sleeve is configured to prevent the catheter from collapsing along the length of the sleeve.

4. The catheter assembly of claim 3, wherein the first end of the expandable sleeve is fixed to the hub.

5. The catheter assembly of claim 3, wherein the second end of the expandable sleeve is tapered.

6. The catheter assembly of claim 1, wherein the second portion of the expandable sleeve comprises a shape-memory material.

7. The catheter assembly of claim 6, further comprising a heat application assembly configured to apply heat to the expandable sleeve such that the sleeve expands from the compressed position to the expanded position.

8. The catheter assembly of claim 6, wherein the shape-memory material comprises at least one of a shape-memory polymer or a shape-memory alloy, wherein the shape-memory polymer comprises at least one of block copolymers, thermoplastic polymers, or thermosetting polymers, and wherein the shape-memory alloy comprises Nitinol.

9. An expandable sleeve for use with an over-the-needle catheter assembly, the sleeve comprising:
    a body comprising a length extending in a longitudinal direction from a first end to a second end, the body configured to fit coaxially around an outer diameter of a catheter of the catheter assembly at a transition location between a hub and the catheter;
    wherein the sleeve is expandable in the longitudinal direction between a compressed position and an expanded position so as to prevent the catheter from collapsing along the length of the sleeve, and
    wherein, in the expanded position, at least a portion of an interior surface of the sleeve contacts an outer diameter of the catheter,
    wherein the expandable sleeve comprises a first portion and a second portion, the first portion being configured with the hub and the second portion being configured with the catheter, wherein the second portion of the expandable sleeve comprises a plurality of bellows to allow the sleeve to expand between the compressed position and the expanded position, and wherein the compressed position maximizes a catheter penetration length.

10. A method for using a catheter assembly to provide treatment to a targeted site within a patient, the method comprising:
    providing a catheter extending in a longitudinal direction from a proximal end to distal end and a hub configured with the proximal end of the catheter;

coaxially mounting an expandable sleeve around an outer diameter the catheter at a transition location between the catheter and the hub such that the expandable sleeve is in an expanded position in the longitudinal direction;

moving the expandable sleeve from the expanded position to a compressed position in the longitudinal direction, wherein the expandable sleeve comprises a first portion and a second portion, the first portion being configured with the hub and the second portion being configured with the catheter, wherein the second portion of the expandable sleeve comprises a plurality of bellows to allow the sleeve to expand between the compressed position and the expanded position; and administering a treatment fluid to the targeted site via the catheter.

11. The method of claim 10, wherein the catheter is coaxially mounted onto a needle and the catheter and the needle are secured together via the hub, wherein the method further comprises:

inserting simultaneously the catheter and the needle into the patient until the distal end of the needle reaches the targeted site, and removing the needle from the catheter while the catheter remains within the patient adjacent to the targeted site before administering the treatment fluid.

12. The method of claim 10, further comprising fitting the first portion of the expandable sleeve over a portion of the hub and fitting the second portion of the expandable sleeve over the outer diameter of the catheter.

13. The method of claim 12, wherein the compressed position maximizes a catheter penetration length.

14. The method of claim 10, wherein the expandable sleeve comprises a total longitudinal length extending from a first end to a second end, and wherein the sleeve is configured to prevent the catheter from collapsing along the length of the sleeve.

15. The method of claim 14, further comprising fixing the first end of the expandable sleeve to the hub.

16. The method of claim 10, wherein moving the expandable sleeve from the expanded position to the compressed position further comprises manually moving the expandable sleeve from the expanded position to the compressed position.

17. The method of claim 10, wherein at least a portion of the expandable sleeve comprises a shape-memory material, wherein moving the expandable sleeve from the expanded position to the compressed position further comprises applying heat to the expandable sleeve.

18. The method of claim 17, wherein applying heat to the expandable sleeve further comprises at least one of the following: generating a current through the sleeve via a nerve stimulation assembly, generating a current through the expandable sleeve via one or more battery devices, submerging at least a portion of the expandable sleeve into a temperature-controlled water, generating friction near the expandable sleeve, or generating vibration near the expandable sleeve via an ultrasound device.

* * * * *